United States Patent [19]

Harris

[11] Patent Number: 5,222,944

[45] Date of Patent: Jun. 29, 1993

[54] SAFETY SYRINGE WITH RETRACTABLE AND LOCKABLE NEEDLE

[76] Inventor: Edmond L. Harris, 318 Barton St., Little Rock, Ark. 72205

[21] Appl. No.: 956,268

[22] Filed: Oct. 5, 1992

[51] Int. Cl.⁵ .............................................. A61M 5/00
[52] U.S. Cl. .................................... 604/110; 604/195; 604/218
[58] Field of Search ............... 604/110, 187, 195, 198, 604/218

[56] References Cited

U.S. PATENT DOCUMENTS

| | | | |
|---|---|---|---|
| 4,731,068 | 3/1988 | Hesse | 604/110 |
| 4,950,251 | 8/1990 | Haining | 604/195 |
| 5,098,402 | 3/1992 | Davis | 604/110 X |

Primary Examiner—John D. Yasko
Attorney, Agent, or Firm—Ray F. Cox, Jr.

[57] ABSTRACT

The present invention provides for retractability of a hypodermic needle and for locking the retracted needle into position by making a limited number of alterations to a standard design of hypodermic syringe. Engagement means are provided on the head of the plunger for engaging and reversibly locking into a complementary recess on the hub housing the needle. The hub is threadedly received into an opening at the forward end of the syringe body. By employing the engagement means on the end of the plunger, the plunger may be used to remove and retract the needle from its fully deployed position into the interior of the body of the syringe. Alternatively, the engagement means can be used to replace the needle into position for reuse. Means for locking the retracted plunger into position include a spiral channel in the body of the syringe which receives one or more elastic radial vanes formed on the plunger. The spiral channel and radial vanes act in the same manner as the threads of a screw in order to reversibly lock the plunger into position. The spiral channel is provided with an end wall which provides a stop mechanism to prevent the plunger from being completely withdrawn once it has been inserted into the body of the syringe.

1 Claim, 2 Drawing Sheets

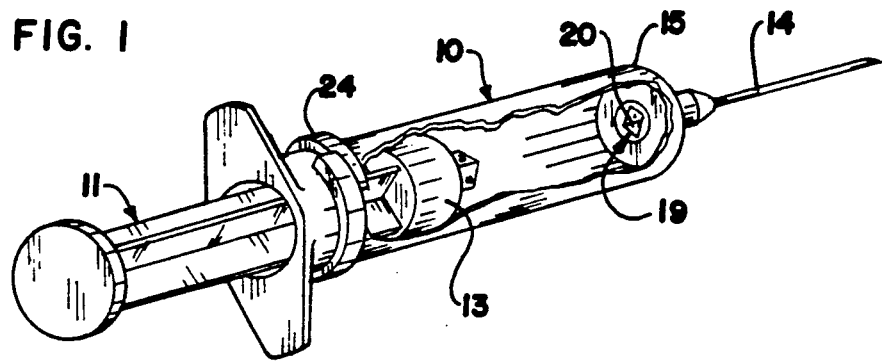
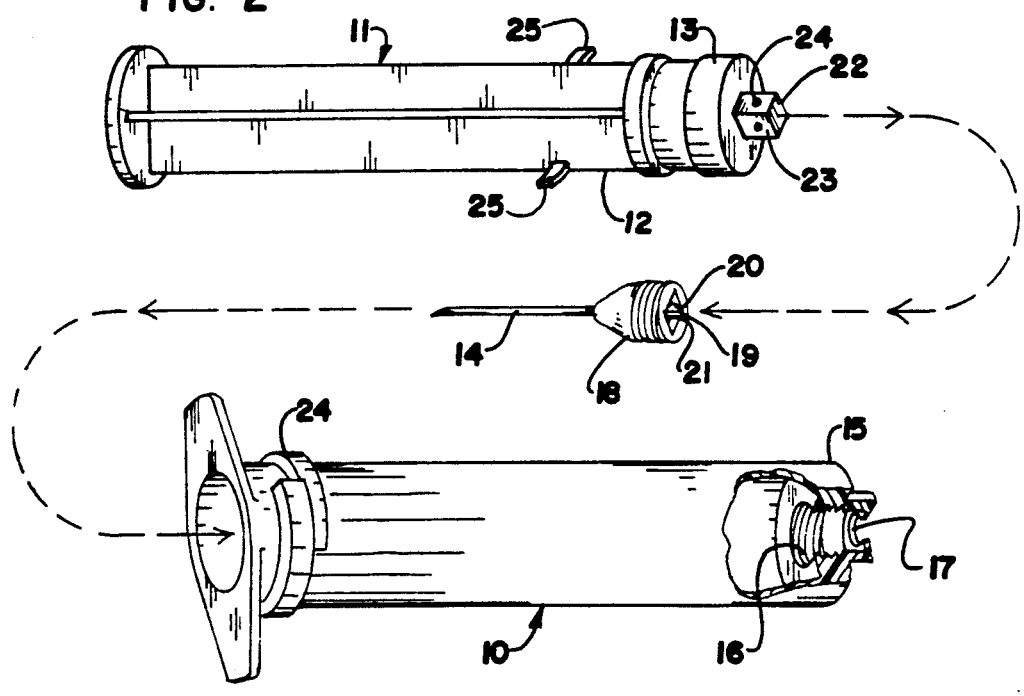

SAFETY SYRINGE WITH RETRACTABLE AND LOCKABLE NEEDLE

BACKGROUND OF THE INVENTION

1. Field of the Invention

This invention relates generally to hypodermic syringes and more particularly to a hypodermic syringe with a needle that may be retracted and locked into a retracted position after use.

2. Description of the Prior Art

Hypodermic syringes are widely used in the medical art. However, in recent years the prevalence of certain types of infectious diseases, such as acquired immune deficiency syndrome and hepatitis have raised concerns regarding the safe use and disposal of hypodermic syringes. Workers in the medical field are well aware that hypodermic syringes are notorious vehicles for the transmission of infectious diseases. If a hypodermic syringe is used on an infected patient, the used syringe becomes a dangerous source of potential infection. Needle pricks are a common hazard to healthcare workers.

In order to overcome this problem, a number of hypodermic syringes have been developed which incorporate means for retracting the needle into the body of the syringe after use so that the risk of contamination by needle prick is substantially reduced thereby allowing the safe disposal of the used syringe.

In order to effect the withdrawal of the used needle into the body of the syringe, the prior art generally shows some means for engaging the needle by the head of the plunger. A large number of variations on this basic concept have been disclosed.

In addition to means for withdrawing the used needle into the body of the syringe, the prior art also discloses a number of syringes having means to lock the needle into a retracted position to prevent reuse. These locking means are generally of two types. One type employs a stop or detent mechanism that permanently locks the plunger into a retracted position within the barrel of the syringe. An example of this type is U.S. Pat. No. 5,026,354 for "Safety Syringe Apparatus" issued to Kocses on Jun. 25, 1991. Another type of locking means involves a mechanism to push the retracted needle to one side, thus making it impossible to reuse the needle after it has been retracted into the body of the syringe. This type of mechanism is disclosed in U.S. Pat. No. 4,986,813 for "Disposable Hypodermic Syringe" issued to Blake, et al. on Jan. 22, 1991.

As an added safety measure some of the prior art discloses means for the plunger to be broken off after withdrawal of the needle into the body of the syringe. Examples of this are found in U.S. Pat. No. 4,790,882 for "Retractable Hypodermic Safety Syringe" issued to Haining on Dec. 13, 1988 and U.S. Pat. No. 4,952,251 for "Simplified Retractable Needle Syringe" issued to Haining on Aug. 21, 1990.

In attempting to find a solution to the problem of a safely disposable retractable needle syringe, the prior art discloses a number of solutions which suffer from their extreme complexity. The prior art retractable needles are often highly complex, at times perhaps, even to the point of being infeasible to manufacture. Furthermore, the prior art retractable needle syringes fail to take into account the need to produce an instrument that is manufacturable and marketable by limiting the alterations to the standard type of manufactured hypodermic syringe to those features absolutely necessary to produce a safe retractable needle syringe. A design of a retractable needle syringe that departs too greatly from the standard design is likely to prove commercially unacceptable.

Furthermore, the prior art has concentrated on the concept of a retractable needle syringe that can only be used one time. Under certain circumstances a multiple-use syringe might be desirable.

SUMMARY OF THE INVENTION

The present invention provides for retractability of the hypodermic needle and locking the retracted needle into position by making a limited number of alterations to a standard design of hypodermic syringe. Briefly engagement means are provided on the head of the plunger for engaging and reversibly locking into a complementary recess on the hub housing the needle. The hub is threadedly received into an opening at the forward end of the syringe body. By employing the engagement means on the end of the plunger, the plunger may be used to remove and retract the needle from its fully deployed position into the interior of the body of the syringe. Alternatively, the engagement means can be used to replace the needle into position for reuse.

The means for locking the retracted plunger into position include a spiral channel in the body of the syringe which receives one or more elastic radial vanes formed on the plunger. The spiral channel and radial vanes act in the same manner as the threads of a screw in order to reversibly lock the plunger into position. The spiral channel is provided with a substantially orthogonal end wall which provides a stop mechanism to prevent the plunger from being completely withdrawn once it has been inserted into the body of the syringe.

It is, therefore, an object of the present invention to produce a retractable needle hypodermic syringe which may be economically and commercially manufacturable with minor modifications to standard commercial designs.

It is also an object of the present invention to provide for a retractable needle hypodermic syringe in which the retracted needle may be locked into position so as to avoid the possible accidental exposure of the contaminated needle.

It is a further object of the present invention to provide for a retractable needle hypodermic syringe which may be configured for multiple use.

DESCRIPTION OF THE DRAWINGS

Other objects and advantages of the present invention will be more fully appreciated upon consideration of the following detailed description of the preferred embodiment in conjunction with the appended drawings of which:

FIG. 1 is a perspective view of the present invention with a cut-away view of the interior of the body of the syringe.

FIG. 2 is an exploded view of the present invention.

DETAILED DESCRIPTION OF THE PREFERRED EMBODIMENT

Figure 3:
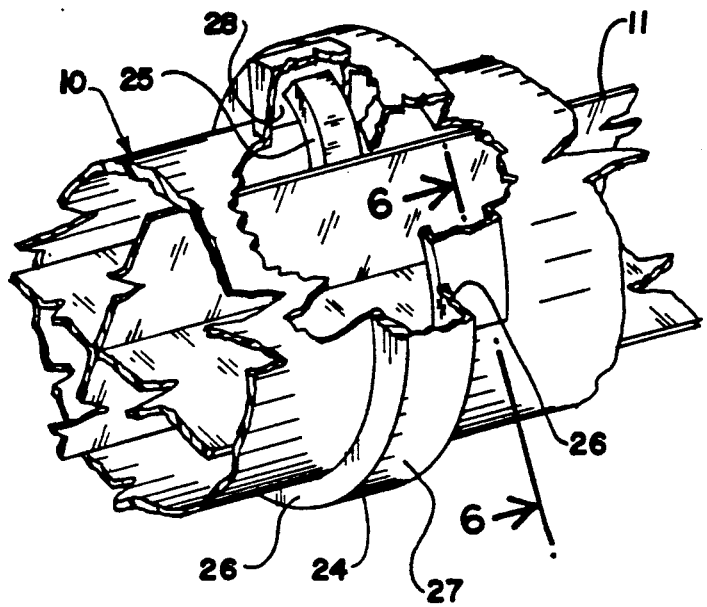
FIG. 3 is a partial view of the plunger and body of the syringe showing a cut-away of the locking mechanism.

The major components of the present invention may be described with reference to FIGS. 1 and 2. The syringe body 10 is a hollow cylinder in which the plunger 11 is able to move freely. The interior end 12 of the plunger 11 is provided with an elastic seal 13 which conforms closely to the interior of the syringe body 10 such that the contents of the syringe are retained without leakage around the plunger 11. A hollow needle 14 is mounted on the forward end 15 of the syringe body 10.

The forward end 15 of the syringe body 10 contains an internally threaded opening 16. The internally threaded opening 16 is provided with a sealing flange 17. The hollow needle 14 is mounted to a threaded hub 18. The needle 14 and threaded hub combination 18 are mounted into the forward end 15 of the syringe body 10 by placing the hollow needle 14 through the threaded opening 16 such that the hollow needle 14 projects forwardly from the syringe body 10. The threaded hub 18 is received into the internally threaded opening 16 so that the hub 18 is sealed against the sealing flange 17. The sealing flange 17 prevents the hub 18 from being threaded completely through the threaded opening 16 as well as providing a sealing effect to retain the contents of the syringe.

The needle 14 and hub 18 combination may be both mounted into the threaded opening 16 and removed therefrom repeatedly using the same mechanism, which is described as follows. The hub 18 contains a rectangular rearward recess 19 which communicates with the hollow interior of the hollow needle 14. The side faces 20 of the rectangular recess 19 each have a depression 21 formed at or near the center of each of the side faces 20. In the preferred embodiment each of the four side faces 20 are square in outline and each of the depressions 21 are semi-spherical. However, minor variations in the size, number, placement and shape of the side faces 20 and the depressions 21 are possible without departing from the spirit and scope of the invention.

As noted previously, the interior end 12 of the plunger 11 is provided with an elastic seal 13. Interiorly of the seal 13 is a rectangular projection 22. The rectangular projection 22 may be formed either as a part of the elastic seal 13 or as part of the body of the plunger 11 and disposed through the center of the elastic seal 13. The rectangular projection 22 is sized to be received within and be complementary to the rearward recess 19 of the hub 18. In the preferred embodiment the projection 22 has four side faces 23 which are square in outline. Each of the side faces 23 has an elastic protrusion 24. The elastic protrusions 24 are located at or near the center of each of the side faces 23 and are further located and sized to be complementary to the depressions 21 formed in the side faces 20 of the rearward recess 19. Due to the elastic nature of the protrusions 24, the projection 22 may be received within the recess 19 so that the protrusions 24 match with and lock into the depressions 20. This locking mechanism is reversible so that the plunger 11 may be engaged and disengaged with the hub 18 as often as needed. For example, the mechanism may be employed to initially assemble the needle 14 and hub 18 combination into the syringe body 10. The plunger 11 may be then disengaged preparatory to the initial use of the syringe. After the syringe has been used all that is necessary to retract the needle 14 into the body 10 is to push the plunger 11 forward so that the projection 22 engages and locks into the recess 19 on the hub 18. By rotating the plunger 11 the hub 18 is unscrewed from the opening 16. By pulling the plunger 11 backwards relative to the body 10, the needle 14 is retracted through the opening 16 into the hollow interior of the body 10. Thus, the potentially dangerous needle has been completely shielded within the body 10 of the syringe.

If for any reason it is desirable to reuse the syringe, the above procedure may be reversed and the hub 18 reinserted and screwed into position in the threaded opening 16. After reinserting the hub 18 into the threaded opening 16, the plunger 11 may be withdrawn so that the projection 22 disengages from the recess 19 at which time the syringe is ready for reuse.

In addition to the ability to retract the needle 14 into the body 10 of the syringe, the retracted needle 14 and plunger 11 may be locked into position in order to avoid accidental redeployment of the needle 14. The locking mechanism comprises a spiral channel 24 disposed in the rearward portion of the syringe body 10 and one or more elastic radial vanes 25 disposed on the forward end 12 of the plunger 11.

The locking mechanism may be described with reference to FIGS. 3 through 6. The spiral channel 24 describes at least one complete circuit of the body 10 of the syringe. The spiral channel 24 is intended to act essentially as the threads of a screw. In the preferred embodiment, the spiral channel 24 comprises a pair of sidewalls 26 which uniformly increase in depth with respect to the syringe body 10 as the sidewalls advance from the forward to the rearward portion of the syringe body 10. The bottom 27 of the spiral channel 24 is thus essentially level with the surface of the syringe body 10 at its most forward position and uniformly moves further away from the surface of the syringe body 10 as the spiral channel 24 progresses toward the rear of the syringe body 10. The spiral channel 24 is terminated in its rearmost portion by an end wall 28, which is essentially orthogonal to the surface of the syringe body 10. As noted above, the spiral channel 24 is intended to function essentially as a screw thread. Therefore, variations on the preferred embodiment which act in essentially the same manner are consistent with the scope of the invention.

Figure 4:
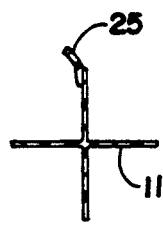
FIGS. 4 and 5 are sectional views of the plunger showing the elastic radial vanes.
Figure 5:
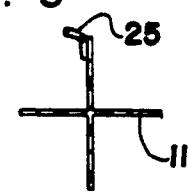

The plunger 11 is provided with at least one elastic radial vane 25. The radial vane 25 is sized and angled so as to ride within the spiral channel 24. The elastic action of the radial vanes 25 is depicted in FIGS. 4 and 5.

Figure 6:
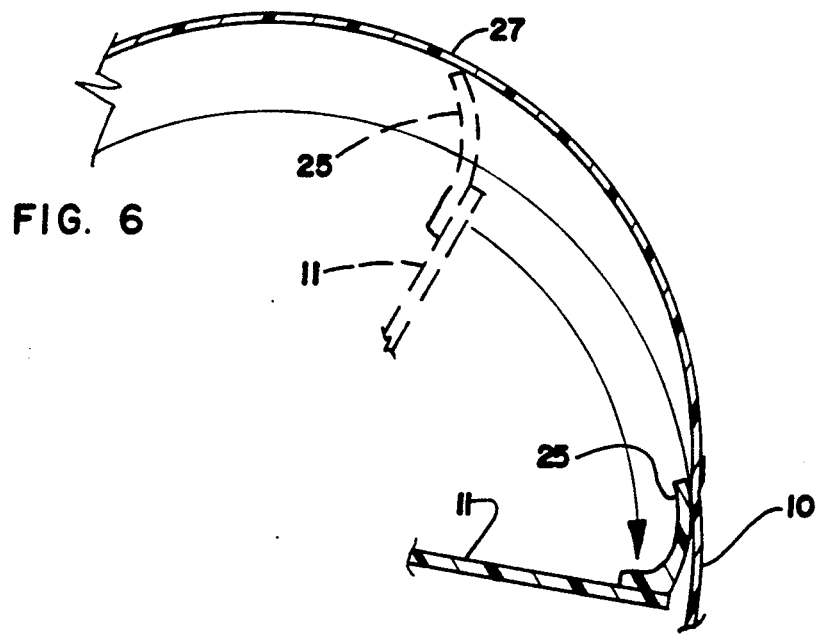
FIG. 6 is a partial sectional view of the body of the syringe showing action of the elastic vanes within the spiral channel.

In use the plunger 11 is inserted into the syringe body 10 by rotating the plunger 11 while simultaneously inserting the forward end of the plunger 11 into the hollow syringe body 10. The elastic nature of the radial vanes 25 allow them to be depressed and inserted into the syringe body 10. The elastic radial vanes 25 ride within and closely conform to the interior surface of the syringe body 10. Upon encountering the spiral channel 24, the elastic vanes 25 tend to fall into the spiral groove 24 and expand radially to the extent allowed by the depth of the bottom wall 27 as shown in FIG. 6. By continuing to rotate the plunger 11, the radial vanes 25 ride out to the end of the spiral groove 24. At this point the plunger may freely be moved up and down within the syringe body 10.

The locking mechanism comes into play when the needle 14 has been retracted into the body of the syringe 10. When the plunger 11 has been retracted such that the radial vanes 25 enter the spiral groove 24, the plunger 11 may be rotated so that the radial vanes 25 are moved rearwardly along the spiral groove 24. However, once one of the radial vanes 25 encounters the end wall 28 the plunger will not be allowed to rotate any further. Furthermore, since the radial vanes 25 are disposed within the spiral groove 24, further retraction of the plunger 11 is thereby prevented. In addition, the deployment of the radial vanes 25 in the spiral groove 24 prevents the plunger from being accidentally jarred so as to project the needle 24 beyond the opening 16 of the syringe body 10. Thus, the used syringe may be safely disposed of at this point.

If it is desired, however, to reuse the syringe, the process described above may be reversed so that the plunger 11 is rotated to advance it out of the locked position at which point the plunger 11 is free to move forward in the syringe body 10 so as to reinsert the needle 14 through the opening 16 and lock the hub 18 into the threaded opening 16 so that the syringe may be reused.

The description of the present invention with respect to a preferred embodiment should not be taken to limit the spirit and scope of the invention as detailed in the appended claims.

What is claimed is:

1. A safety syringe with retractable and lockable needle, comprising:
   a hollow cylindrical syringe body having a forward end and a rearward end;
   a plunger slidably disposed within said syringe body;
   elastic sealing means at the interior end of said plunger;
   engagement means formed at said interior end, said engagement means comprising a rectangular projection having four side faces, each of said side faces having an elastic protrusion;
   said syringe body further having an internally threaded forward opening and a sealing flange;
   a hypodermic needle mounted to an externally threaded hub sized so that said hub may be threadedly received into said forward opening and sealed against said sealing flange with said hypodermic needle projecting forwardly therefrom;
   said hub further having a rectangular rearward recess shaped to receive said rectangular projection, said rectangular rearward recess further having four side faces with a depression formed in each of said side faces of said recess sized and positioned to receive and reversibly lockingly engage with said elastic protrusions of said rectangular projection of said plunger;
   said syringe body further having a spiral channel formed at said rearward end comprising at least one complete circuit of said syringe body, said channel further comprising a bottom surface, a pair of side walls uniformly rearwardly increasing in depth with respect to said syringe body, and an end wall terminating said channel, said end wall being substantially orthogonal to said syringe body; and
   said plunger further having at least one elastic radial vane formed at the interior end of said plunger, said vane being sized and angled to ride within said spiral channel and disposed so that said plunger may be inserted into said syringe body by rotationally advancing said plunger in one direction only and after being inserted into said syringe body, said radial vane is received into said channel such that said plunger cannot thereafter be retracted beyond the point at which said radial vane encounters said end wall.

* * * * *